US010300064B2

(12) United States Patent
Li et al.

(10) Patent No.: US 10,300,064 B2
(45) Date of Patent: May 28, 2019

(54) ORGANIC COMPOUNDS

(71) Applicant: INTRA-CELLULAR THERAPIES, INC., New York, NY (US)

(72) Inventors: Peng Li, New Milford, NJ (US); Hailin Zheng, Teaneck, NJ (US); Gretchen Snyder, New York, NY (US); Lawrence P. Wennogle, Hillsborough, NJ (US); Joseph Hendrick, Bridgeport, CT (US)

(73) Assignee: INTRA-CELLULAR THERAPIES, INC., New York, NY (US)

( * ) Notice: Subject to any disclaimer, the term of this patent is extended or adjusted under 35 U.S.C. 154(b) by 0 days.

(21) Appl. No.: 15/533,527

(22) PCT Filed: Dec. 7, 2015

(86) PCT No.: PCT/US2015/064324
§ 371 (c)(1),
(2) Date: Jun. 6, 2017

(87) PCT Pub. No.: WO2016/090380
PCT Pub. Date: Jun. 9, 2016

(65) Prior Publication Data
US 2017/0360792 A1     Dec. 21, 2017

Related U.S. Application Data

(60) Provisional application No. 62/088,541, filed on Dec. 6, 2014.

(51) Int. Cl.
| *C07D 487/04* | (2006.01) |
| *C07D 403/14* | (2006.01) |
| *C07D 401/14* | (2006.01) |
| *A61K 31/519* | (2006.01) |
| *A61P 25/28* | (2006.01) |
| *A61P 9/12* | (2006.01) |
| *C07D 231/06* | (2006.01) |
| *C07D 231/54* | (2006.01) |

(52) U.S. Cl.
CPC .............. *A61K 31/519* (2013.01); *A61P 9/12* (2018.01); *A61P 25/28* (2018.01); *C07D 231/06* (2013.01); *C07D 231/54* (2013.01); *C07D 401/14* (2013.01); *C07D 403/14* (2013.01); *C07D 487/04* (2013.01); *A61K 2300/00* (2013.01)

(58) Field of Classification Search
CPC .. C07D 487/04; C07D 401/14; C07D 403/14; C07D 401/13; A61K 31/519; A61P 25/28; A61P 9/12
USPC ........................................ 544/262; 514/262.1
See application file for complete search history.

(56) References Cited

U.S. PATENT DOCUMENTS

| 4,766,122 | A  | 8/1988  | Coates |
| 5,294,612 | A  | 3/1994  | Bacon et al. |
| 5,393,755 | A  | 2/1995  | Neustadt et al. |
| 5,824,683 | A  | 10/1998 | McKittrick et al. |
| 5,861,396 | A  | 1/1999  | Niewohner et al. |
| 5,939,419 | A  | 8/1999  | Tulshian et al. |
| 6,013,621 | A  | 1/2000  | Nishi et al. |
| 6,492,371 | B2 | 6/2002  | Roylance et al. |
| 6,756,373 | B1 | 6/2004  | Allerton et al. |
| 6,969,719 | B2 | 11/2005 | Asberom et al. |
| 7,153,824 | B2 | 12/2006 | Palmer et al. |
| 7,964,607 | B2 | 6/2011  | Verhoest et al. |
| 8,193,356 | B2 | 6/2012  | Kanazawa et al. |
| 8,273,750 | B2 | 9/2012  | Li et al. |
| 8,273,751 | B2 | 9/2012  | Li et al. |
| 8,536,159 | B2 | 9/2013  | Li et al. |
| 8,633,180 | B2 | 1/2014  | Li et al. |
| 8,664,207 | B2 | 3/2014  | Li et al. |
| 8,829,010 | B2 | 3/2014  | Helal et al. |
| 8,697,710 | B2 | 4/2014  | Li et al. |
| 8,829,008 | B2 | 9/2014  | Li et al. |
| 8,846,693 | B2 | 9/2014  | Li et al. |
| 8,859,564 | B2 | 10/2014 | Li et al. |
| 8,927,556 | B2 | 1/2015  | Li et al. |
| 9,000,001 | B2 | 4/2015  | Li et al. |
| 9,006,258 | B2 | 4/2015  | Fienberg et al. |
| 9,073,936 | B2 | 7/2015  | Li et al. |
| 9,157,906 | B2 | 10/2015 | Greengard et al. |
| 9,198,924 | B2 | 12/2015 | Mates et al. |
| 9,255,099 | B2 | 2/2016  | Li et al. |
| 9,403,836 | B2 | 8/2016  | Li et al. |
| 9,468,637 | B2 | 10/2016 | Fienberg et al. |
| 9,546,175 | B2 | 1/2017  | Li et al. |
| 9,556,186 | B2 | 1/2017  | Li et al. |
| 9,598,426 | B2 | 3/2017  | Li et al. |
| 9,624,230 | B2 | 4/2017  | Li et al. |
| 2002/0198377 | A1 | 12/2002 | Niewohner et al. |
| 2003/0162782 | A1 | 8/2003  | Grossman et al. |
| 2005/0075795 | A1 | 4/2005  | Pandit et al. |
| 2007/0208029 | A1 | 9/2007  | Barlow et al. |
| 2008/0176961 | A1 | 7/2008  | Greengard et al. |
| 2008/0193964 | A1 | 8/2008  | Greengard et al. |
| 2008/0194592 | A1 | 8/2008  | Mates et al. |
| 2010/0093782 | A1 | 4/2010  | Kanazawa et al. |
| 2010/0120762 | A1 | 5/2010  | Stange et al. |
| 2011/0009322 | A1 | 1/2011  | Sharif et al. |
| 2011/0312978 | A1 | 12/2011 | Davis et al. |
| 2012/0220624 | A1 | 8/2012  | Siu et al. |

(Continued)

FOREIGN PATENT DOCUMENTS

DE    19931206    1/2001
EP    0201188     12/1986

(Continued)

OTHER PUBLICATIONS

Freshney et al.,Culture of Animal Cells, A Manual of Basic Technique, Alan R. Liss, Inc., 1983, New York, p. 4.*

(Continued)

*Primary Examiner* — Venkataraman Balasubramanian
(74) *Attorney, Agent, or Firm* — Hoxie & Associates LLC

(57) ABSTRACT

The present invention relates to certain PDE2 inhibitory compounds, in free or salt form, pharmaceutical compositions containing such compounds and methods for the treatment of PDE2 mediated disorders.

8 Claims, 1 Drawing Sheet

(56) References Cited

U.S. PATENT DOCUMENTS

| | | |
|---|---|---|
| 2013/0018063 A1 | 1/2013 | Li et al. |
| 2014/0005155 A1 | 1/2014 | Li et al. |
| 2014/0011783 A1 | 1/2014 | Li et al. |
| 2014/0148421 A1 | 5/2014 | Li et al. |
| 2014/0194396 A1 | 7/2014 | Li et al. |

FOREIGN PATENT DOCUMENTS

| | | |
|---|---|---|
| EP | 0379917 | 8/1990 |
| EP | 0911333 | 4/1999 |
| EP | 1548011 | 6/2005 |
| EP | 1749824 | 2/2007 |
| EP | 1925617 | 5/2008 |
| JP | 5068857 | 3/2011 |
| KR | 10-1991-0006866 | 9/1991 |
| WO | WO 1991/019717 | 12/1991 |
| WO | WO 1994/019351 | 9/1994 |
| WO | WO 1998/032755 | 7/1998 |
| WO | WO 1998/046606 | 10/1998 |
| WO | WO 1998/052568 | 11/1998 |
| WO | WO 2002/009713 | 2/2002 |
| WO | WO 2002/050078 | 6/2002 |
| WO | WO 2002/068423 | 9/2002 |
| WO | WO 2003/002567 | 1/2003 |
| WO | WO 2003/020702 | 3/2003 |
| WO | WO 2003/020724 | 3/2003 |
| WO | WO 2003/042216 | 5/2003 |
| WO | WO 2004/041258 | 5/2004 |
| WO | WO 2004/089953 | 10/2004 |
| WO | WO 2005/041957 | 5/2005 |
| WO | WO 2005/061497 | 7/2005 |
| WO | WO 2005/083069 | 9/2005 |
| WO | WO 2006/024640 | 3/2006 |
| WO | WO 2006/072612 | 7/2006 |
| WO | WO 2006/072615 | 7/2006 |
| WO | WO 2006/133261 | 12/2006 |
| WO | WO 2007/143705 | 12/2007 |
| WO | WO 2008/063505 | 5/2008 |
| WO | WO 2008/070095 | 6/2008 |
| WO | WO 2009/073210 | 6/2009 |
| WO | WO 2009/075784 | 6/2009 |
| WO | WO 2010/054253 | 5/2010 |
| WO | WO 2010/054260 | 5/2010 |
| WO | WO 2010/062366 | 6/2010 |
| WO | WO 2010/065147 | 6/2010 |
| WO | WO 2010/065148 | 6/2010 |
| WO | WO 2010/065149 | 6/2010 |
| WO | WO 2010/065151 | 6/2010 |
| WO | WO 2010/065152 | 6/2010 |
| WO | WO 2010/065153 | 6/2010 |
| WO | WO 2010/098839 | 9/2010 |
| WO | WO 2010/132127 | 11/2010 |
| WO | WO 2011/011312 | 1/2011 |
| WO | WO 2011/043816 | 4/2011 |
| WO | WO 2011/153129 | 12/2011 |
| WO | WO 2011/153135 | 12/2011 |
| WO | WO 2011/153136 | 12/2011 |
| WO | WO 2011/153138 | 12/2011 |
| WO | WO 2012/104293 | 8/2012 |
| WO | WO 2012/114222 | 8/2012 |
| WO | WO 2012/168817 | 12/2012 |
| WO | WO 2012/171016 | 12/2012 |
| WO | WO 2013/000924 | 1/2013 |
| WO | WO 2013/034755 | 3/2013 |
| WO | WO 2013/034758 | 3/2013 |
| WO | WO 2013/034761 | 3/2013 |
| WO | WO 2013/192556 | 12/2013 |
| WO | WO 2014/151409 | 9/2014 |
| WO | WO 2014/154586 | 10/2014 |

OTHER PUBLICATIONS

Dermeret al., Bio/Technology, 1994, 12:320.Dermeret al., Bio/Technology, 1994, 12:320.*

Ahlstrom et al., "Inactivation of Atrial Natriuretic Factor-Stimulated Cyclic Guanosine 39, 59-Monophosphate (cGMP) in UMR-106 Osteoblast-like Cells," *Biochemical Pharmacology*, vol. 59: 1133-1139 (2000).
Ahn, H. et al., "Potent Tetracyclic Guanine Inhibitors of PDE1 and PDE5 Cyclic Guanosine Monophosphate Phosphodiesterases with Oral Antihypertensive Activity," *J. Med. Chem.*, vol. 40(14): 2196-2210 (1997).
Aswar, "Anti-Cataleptic Activity of Various Extracts of Ocimum Sanctum," *International Journal of Pharma. Research and Development*, vol. 2(6): 1-7 (2010).
Banker, G.S. et al., *Modern Pharmaceutics*, Marcel Dekker, New York, 1996.
Bender, A.T. et al., "Cyclic Nucleotide Phosphodiesterases: Molecular Regulation to Clinical Use," *Pharmacol. Rev.*, vol. 58: 488-520 (2006).
Boess et al., "Inhibition of phosphodiesterase 2 increases neuronal cGMP, synaptic plasticity and memory performance," *Neuropharmacology*, vol. 47: 1081-1092 (2004).
Boyd et al., "Dopamine receptor signaling and current and future antipsychotic drugs," *Handbook Exp Pharmacol.*, vol. 212: 53-86 (2012).
Brandon et al., "Potential CNS Applications for Phosphodiesterase Enzyme Inhibitors," *Annual Reports in Medicinal Chemistry*, vol. 42: 1-10 (2007).
Bubb et al., "Inhibition of Phosphodiesterase 2 Augments cGMP and cAMP Signaling to Ameliorate Pulmonary Hypertension," *Circulation*, 496-507 (2014).
Chalimoniuk, "Upregulation of guanylyl cyclase expression and activity in striatum of MPTP-induced parkinsonism in mice," *Biochem. Biophys. Res. Commun.*, vol. 324(1): 118-126 (2004).
DE19931206, Stief Christian, "Relaxing, or increasing cyclic adenosine monophosphate concentration in smooth muscular tissue, e.g. by administration of cAMP phosphodiesterase inhibitors, dipyridamole or sildenafil," Jan. 11, 2001, English language machine translation of abstract, Espacenet, date obtained: Sep. 6, 2017, 2 pages, <URL: https://worldwide.espacenet.com/publicationDetails/biblio?CC=DE&NR=19931206A1&KC=A1&FT=D&ND=3&date=20010111&DB=&locale=en_EP>.
Deshmukh, et al., "Amelioration of intracerebroventricular streptozotocin induced cognitive dysfunction and oxidative stress by vinpocetine—a PDE1 inhibitor," *European Journal of Pharmacology*, vol. 620(1-3): 49-56 (2009).
Dewald, H.A. et al., "Synthesis and Potential Antipsychotic Activity of 1 H-Imidazo[1,2-c]pyrazolo[3,4-e]pyrimidines," *J. Med. Chem.*, vol. 31: 454-461 (1988).
Domek-Lopacinska et al., "The effect of selective inhibition of cyclic GMP hydrolyzing phosphodiesterases 2 and 5 on learning and memory processes and nitric oxide synthase activity in brain during aging," *Brain Research*, vol. 1216: 68-77 (2008).
Ehrman et al., "Phosphodiesterase 1B differentially modulates the effects of methamphetamine on locomotor activity and spatial learning through DARPP32-dependent pathways: evidence from PDE1B-DARPP32 double-knockout mice," *Genes Brain Behav.*, vol. 5(7): 540-551 (2006).
Fienberg, A.A. et al., "DARPP-32: Regulator of the Efficacy of Dopaminergic Neurotransmission," *Science*, vol. 281: 838-842 (1998).
Filgueiras et al., "Phosphodiesterase type 1 inhibition improves learning in rats exposed to alcohol during the third trimester equivalent of human gestation," *Neuroscience Letters*, vol. 473(3): 202-207 (2010).
Gomez et al., "PDE2 inhibition: Potential for the treatment of cognitive disorders," *Bioorganic & Medicinal Chemistry Letters*, vol. 23: 6522-6527 (2013).
Greengard, P. et al., "Beyond the Dopamine Receptor: the DARPP-32/Protein Phosphatase-1 Cascade," *Neuron*, vol. 23: 435-447 (1999).
International Search Report for International Application No. PCT/US2015/010697, dated Apr. 6, 2015, 2 pages.
International Search Report for International Application No. PCT/US2015/064324, dated Feb. 12, 2016, 3 pages.
International Search Report for International Application No. PCT/US2015/064331, dated Feb. 12, 2016, 3 pages.

(56) References Cited

OTHER PUBLICATIONS

Han, P. et al., "The Calcium/Calmodulin-dependent Phosphodiesterase PDE1C Down-regulates Glucose-induced Insulin Secretion," *J. Bio. Chem.*, vol. 274(32): 22337-22344 (1999).

Hulley et al., "Cyclic AMP promotes the survival of dopaminergic neurons in vitro and protects them from the toxic effects of MPP+," *J. Neural Transm. Suppl.*, vol. 46: 217-228 (1995).

Jiang, M. et al., "Chemoenzymatic Asymmetric Total Synthesis of Phosphodiesterase Inhibitors: Preparation of a Polycyclic Pyrazolo[3,4-d]pyrimidine from an Acylnitroso Diels-Alder Cycloadduct-Derived Aminocyclopentenol," *J. Org. Chem.*, vol. 70: 2824-2827 (2005).

JP5068857, Intra-Cellular Therapies, Inc., "Organic Compounds," Mar. 3, 2011, English language machine translation of abstract, Espacenet, date obtained: Sep. 6, 2017, 1 page, <URL: https://worldwide.espacenet.com/publicationDetails/biblio?CC=JP&NR=2011506321A&KC=A&FT=D&ND=3&date=20110303&DB=&locale=en_EP>.

Kakkar et al., "Amantadine: an antiparkinsonian agent inhibits bovine brain 60 kDa calmodulin-dependent cyclic nucleotide phosphodiesterase isozyme," *Brain Res.*, vol.749(2): 290-294 (1997).

Kakkar et al., "Calmodulin-dependent cyclic nucleotide phosphodiesterase (PDE1)," *Cell Mol. Life Sci.*, vol. 55(8-9): 1164-86 (1999).

Kakkar et al., "Inhibition of Bovine Brain Calmodulin-Dependent Cyclic Nucleotide Phosphodiesterase Isozymes by Deprenyl," *Life Sciences*, vol. 59(21): 337341 (1996).

Klaissle, "Physical activity and environmental enrichment regulate the generation of neural precursors in the adult mouse substantia nigra in a dopamine-dependent manner," *BMC Neurosci.*, vol. 31: 13-132 (2012).

Kleppisch, "Phosphodiesterases in the central nervous system," *Handb Exp Pharmacol.*, vol. 191: 71-92 (2009).

Laddha et al., "A new therapeutic approach in Parkinson's disease: Some novel quinazoline derivatives as dual selective phosphodiesterase 1 inhibitors and anti-inflammatory agents," *Bioorganic & Medicinal Chemistry*, vol. 17(19): 6796-6802 (2009).

Mani, S.K. et al., "Requirement for DARPP-32 in Progesterone-Facilitated Sexual Receptivity in Female Rats and Mice," *Science*, vol. 287: 1053 (2000).

Masood et al., "Anxiolytic Effects of Phosphodiesterase-2 Inhibitors Associated with Increased cGMP Signaling," *The Journal of Pharmacology and Experimental Therapeutics*, vol. 331(2): 690-699 (2009).

Masood et al., "Reversal of Oxidative Stress-Induced Anxiety by Inhibition of Phosphodiesterase-2 in Mice," *J Pharmacol Exp Ther.*, vol. 326(2): 369-379 (2008).

Medina, "Therapeutic Utility of Phosphodiesterase Type 1 Inhibitors in Neurological Conditions," *Front. Neurosci.*, vol. 5(21): 6 (2011).

Murray, F. et al., "Expression and activity of cAMP phosphodiesterase isoforms in pulmonary artery smooth muscle cells from patients with pulmonary hypertension: role for PDE1," *Am. J. Physiol. Lung Cell Mol. Physiol.*, vol. 292: L294-L303 (2007).

Nishi, A. et al., "Advanced Research on Dopamine Signaling to Develop Drugs for the Treatment of Mental Disorders: Biochemical and Behavioral Profiles of Phosphodiesterase Inhibition in Dopaminergic Neurotransmission," *J. Pharmacol. Sci.*, vol. 114: 6-16 (2010).

Polli, J.W. et al., "Expression of a Calmodulin-Dependent Phosphodiesterase Isoform (PDE1B1) Correlates With Brain Regions Having Extensive Dopaminergic Innervation," *The Journal of Neuroscience*, vol. 14: 1251-1261 (1994).

Reed, T.M. et al., "Phosphodiesterase 1B Knock-Out Mice Exhibit Exaggerated Locomotor Hyperactivity and DARPP-32 Phosphorylation in Response to Dopamine Agonists and Display Impaired Spatial Learning," *The Journal of Neuroscience*, vol. 22(12): 5188-5197 (2002).

Reierson et al., "Repeated antidepressant therapy increases cyclic GMP signaling in rat hippocampus," *Neuroscience Letters*, vol. 466(3): 149-153 (2009).

Rybalkin, S.D. et al., "Cyclic GMP Phosphodiesterases and Regulation of Smooth Muscle Function," *Circ. Res.*, vol. 93: 280-291 (2003).

Schmidt, "Phosphodiesterase inhibitors as potential cognition enhancing agents," *Current Topics in Medicinal Chemistry*, vol. 10(2): 222-230 (2010).

Sharma et al., "Regulation of Calmodulin-Stimulated Cyclic Nucleotide Phosphodiesterase (PDE1): Review," *International Journal of Molecular Medicine*, vol. 18: 95-105 (2006).

Shimizu, K. et al., "Calmodulin-Dependent Cyclic Nucleotide Phosphodiesterase (PDE1) is a Pharmacological Target of Differentiation-Inducing Factor-1, an Antitumor Agent Isolated from Dictyostelium," *Cancer Research*, vol. 64: 2568-2571 (2004).

Shook et al., "Design and Characterization of Optimized Adenoside A2A/A1 Receptor Antagonists for the Treatment of Parkinson's Disease," *J. Med. Chem.*, vol. 1-47 (2012).

Suvarna et al., "Hydrolysis of N-Methyl-D-aspartate Receptor-Stimulated cAMP and cGMP by PDE4 and PDE2 Phosphodiesterases in Primary Neuronal Cultures of Rat Cerebral Cortex and Hippocampus," *The Journal of Pharmacology and Experimental Therapeutics*, vol. 302(1): 249-256 (2002).

Van Staveren et al., "The effects of phosphodiesterase inhibition on cyclic GMP and cyclic AMP accumulation in the hippocampus of the rat," *Brain Research*, vol. 888: 275-286 (2001).

Vatter, S. et al., "Differential Phosphodiesterase Expression and Cytosolic Ca in Human CNS Tumour Cells and in Non-Malignant and Malignant Cells of Rat Origin," *J. of Neurochemistry*, vol. 93: 321-329 (2005).

Velardez et al., "Role of phosphodiesterase and protein kinase G on nitric oxide-induced inhibition of prolactin release from the rat anterior pituitary," *European Journal of Endocrinology*, vol. 143: 279-284 (2000).

Wakabayashi et al., "Involvement of Phosphodiesterase Isozymes in Osteoblastic Differentiation," vol. 17(2): 249-256 (2002).

Wolff, M.E. *Burger's Medicinal Chemistry and Drug Discovery*, Fifth Ed., vol. 1: Principles and Practice, John Wiley & Sons, 975 (1995).

Xia, Y. et al., "Synthesis and Evaluation of Polycyclic Pyrazolo[34-d]pyrimidines as PDE1 and PDE5 cGMP Phosphodiesterase Inhibitors," *J. Med. Chem.*, vol. 40. 4372-4377 (1997).

Xu et al., "Phosphodiesterase-2 inhibitor reverses corticosterone-induced neurotoxicity and related behavioural changes via cGMP/PKG dependent pathway," *International Journal of Neuropsychopharmacology*, vol. 16: 835-847 (2013).

Xu et al., "The effects of curcumin on depressive-like behaviors in mice," *European Journal of Pharmacology*, vol. 518(1): 40-46 (2005).

Côté et al., "Comparative Involvement of Cyclic Nucleotide Phosphodiesterases and Adenylyl Cyclase on Adrenocorticotropin-Induced Increase of Cyclic Adenosine Monophosphate in Rat and Human Glomerulosa Cells," *Endocrinology*, 140(8): 3594-3601 (1999).

EP0379917, Bayer AG, "Optically active (meth)acrylic-acid derivatives, their preparation, their polymerization into optically active polymers and their use," Aug. 1, 1990, English language machine translation of abstract, Espacenet, date obtained: Feb. 23, 2018, 2 pages: <URL: https://worldwide.espacenet.com/publicationDetails/biblio?CC=EP&NR=0379917A2&KC=A2&FT=D&ND=3&date=19900801&DB=&locale=en_EP>.

Nishi et al., "Glutamate regulation of DARPP-32 phosphorylation in neostriatal neurons involves activation of multiple signaling cascades," PNAS, 102(4): 1199-1204 (2005).

Nishi, A., et al., "Distinct Roles of PDE4 and PDE10A in the Regulation of cAMP/PKA Signaling the Striatum," The Journal of Neuroscience, 28(42): 10460-10471 (2008).

Baliga, R.S., et al., "Phosphodiesterase 2 inhibition preferentially promotes NO/guanylyl cyclase/cGMP signaling to reverse the development of heart failure," PNAS, 115(31): E7428-E7437 (2018).

\* cited by examiner

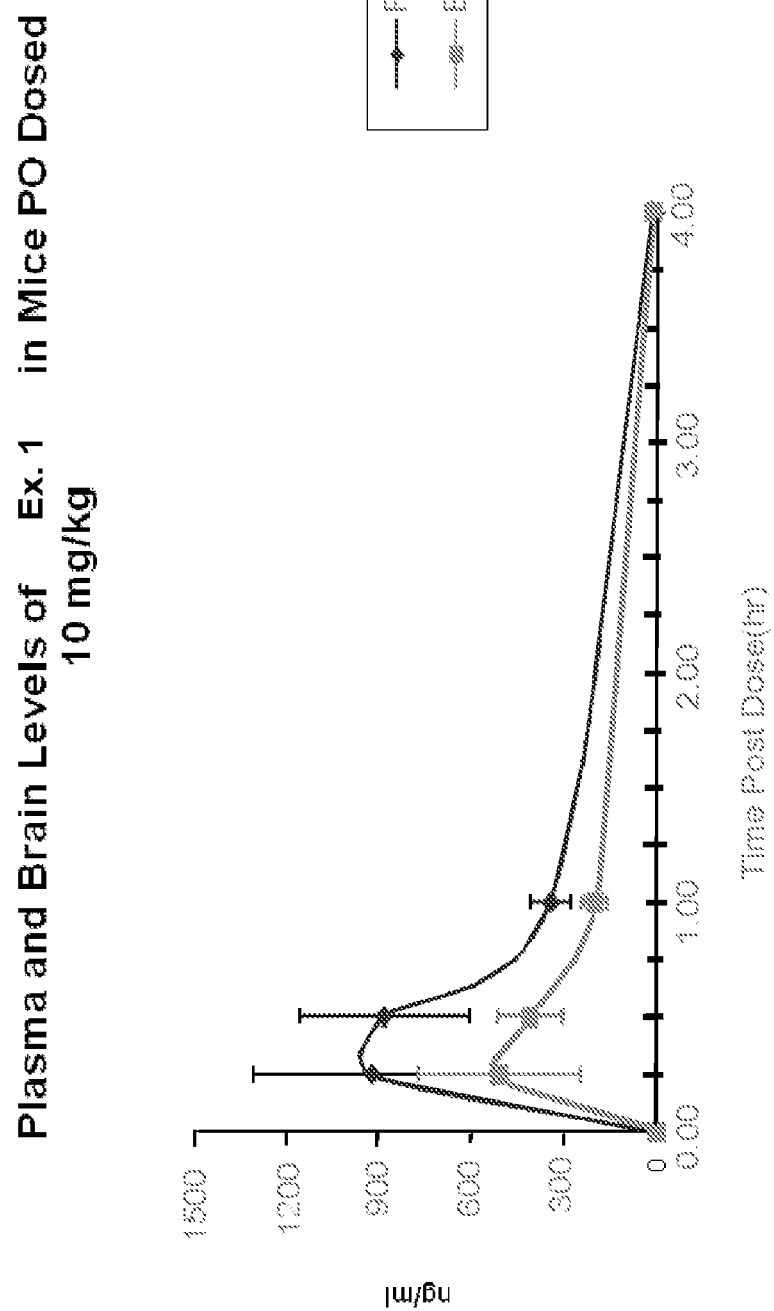

ORGANIC COMPOUNDS

CROSS-REFERENCE TO RELATED APPLICATIONS

This application is a United States Application under 35 U.S.C. 371 claiming benefit of PCT Application No. PCT/US2015/064324, filed on Dec. 7, 2015, which claims priority to U.S. Provisional Application No. 62/088,541 filed Dec. 6, 2014, the contents of which are hereby incorporated by reference in their entirety.

TECHNICAL FIELD

The present invention relates to PDE2 inhibitory compounds of Formula I as described below, their use as pharmaceuticals and pharmaceutical compositions comprising them. These compounds are useful e.g., in the treatment of PDE2-mediated disorders such as anxiety, depression, autism spectrum disorder (ASD), schizophrenia and cognitive impairment.

BACKGROUND OF THE INVENTION

PDE2 is a 105-KDa homodimer that is expressed in a wide variety of tissues and cell types including brain (including hippocampus, striatum and prefrontal cortex), heart, platelets, endothelial cells, adrenal glomerulosa cells and macrophages. Although cGMP is the preferred substrate and effector molecule for this enzyme, PDE2 hydrolyzes both cyclic adenosine monophosphate (cAMP) and cyclic guanosine monophosphate (cGMP) and is thought to be involved in a number of physiological processes. In particular, it has been shown that inhibition of nitric oxide synthase (NOS), which reduces cGMP signaling, attenuates the behavioral effects of the benzodiazepine chlordiazepoxide, an anxiolytic compound. Also, commercially-available tool inhibitors of PDE2 such as Bay 60-7550 has been shown to increase qcyclic nucleotide levels in the brain and have significant anti-anxiety and anti-depressant effects in normal and stressed rodents (Xu et al., *Eur. J. Pharmacol.* (2005) 518:40-46; Masood et al., *J. Pharmacol. Exp. Ther.* (2008) 326:369-379; Masood et al., *JPET* (2009) 331:690-699; Xu et al., *Intl. J. Neuropsychopharmacol.* (2013) 16:835-847). Inhibition of PDE2 by Bay 60-7550 have also been shown to elevate cGMP and cAMP levels in stimulated primary neuronal cultures in a dose responsive manner; enhance LTP in hippocampal slice preparations in response to electrical stimulation; enhance learning in novel object recognition animal model and a social recognition task in rats; improve acquisition and consolidation phases of novel object memory in age impaired rats; improve performance on object location and recognition tasks when administered after training. Gomez et al., *Bioorg. Med. Chem. Lett.* (2013) 23:6522-6527. Bay 60-7550 has also been shown to improve cognition and memory function in rats through the enhancement of nNOS activity in the brain. (Domek-Lopacinska et al. (2008) *Brain Res.* 1216:68-77). Therefore, PDE2 plays an important role in effective behaviors and cognitive function.

In addition to effective behavior and cognitive function, it has been observed that in endothelial cells, PDE2A mRNA and activity are highly induced in response to tumor necrosis factor-α stimulation in vitro. Selective inhibition of PDE2 activity with 9-(6-phenyl-2-oxohex-3-yl)-2-(3,4-dimethoxybenzyl)-purin-6-one (PDP) greatly alters the barrier function of endothelial cells, suggesting that PDE2 is likely to play an important role in regulating fluid and protein integrity of the circulatory system under pathological conditions. Therefore, PDE2 may be a good pharmacological target for sepsis or in more localized inflammatory responses.

In a recent study, PDE2 inhibition has also been shown to elicit pulmonary dilation, prevents pulmonary vascular remodeling and reduces the right ventricular hypertrophy characteristic of pulmonary hypertension, suggesting therapeutic potential of PDE2 inhibition in pulmonary hypertension. Bubb et al., "Inhibition of Phosphodiesterase 2 Augments cGMP and cAMP Signaling to Ameliorate Pulmonary Hypertension", Circulation, Aug. 5, 2014, p. 496-507, DOI: 10.1161/CIRCULATIONAHA.114.009751.

Despite the promising preclinical data and the identification of PDE2 as a promising drug target, no PDE2 inhibitors are currently known to be under clinical investigation due in part to the poor metabolic stability and brain penetrance of existing PDE2 compounds. There is thus a need for compounds that selectively inhibit PDE2 activity while demonstrate superior biophysical properties.

SUMMARY OF THE INVENTION

The disclosure provides novel compounds having potent and selective PDE2 inhibitory properties with improved orally availability and brain access. Therefore, in the first aspect, the disclosure provides a compound of Formula I:

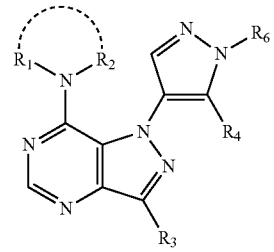

Formula I wherein
(i) $R_1$ and $R_2$ together with the nitrogen atom form a heteroC$_{3-7}$cycloalkyl (e.g., forms an azetidin-1-yl);
(ii) $R_3$ is H or C$_{1-4}$ alkyl (e.g., methyl);
(iii) $R_4$ is hetroaryl or aryl (e.g., phenyl) optionally substituted with one or more groups selected from C$_{1-4}$ alkyl (e.g., ethyl), C$_{3-7}$ cycloalkyl (e.g., cyclopropyl), C$_{1-4}$alkoxy (e.g., methoxy) and haloC$_{1-4}$alkyl (e.g., trifluoromethyl);
(iv) $R_6$ is H or C$_{1-4}$ alkyl (e.g., methyl);
in free or salt form.

The disclosure further provides the compound of Formula I as follows:
1.1 Formula I, wherein $R_1$ and $R_2$ together with the nitrogen atom form a heteroC$_{3-7}$cycloalkyl (e.g., azetidin-1-yl);
1.2 Formula 1.1, wherein $R_1$ and $R_2$ together with the nitrogen atom form an azetidin-1-yl;
1.3 Formula I, or any of 1.1-1.2, wherein $R_3$ is H or C$_{1-4}$alkyl (e.g., methyl);
1.4 Formula I, or any of 1.1-1.2, wherein $R_3$ is C$_{1-4}$alkyl (e.g., methyl);
1.5 Formula I or any of 1.1-1.4, wherein $R_4$ is hetroaryl or aryl (e.g., phenyl) optionally substituted with one or more groups selected from C$_{1-4}$alkyl (e.g., ethyl), C$_{3-7}$cycloalkyl (e.g., cyclopropyl), C$_{1-4}$ alkoxy (e.g., methoxy) and haloC$_{1-4}$alkyl (e.g., trifluoromethyl);

1.6 Formula I or any of 1.1-1.4, wherein R$_4$ is aryl (e.g., phenyl) substituted with one or more groups selected from C$_{1-4}$alkyl (e.g., ethyl), C$_{3-7}$ cycloalkyl (e.g., cyclopropyl), C$_{1-4}$alkoxy (e.g., methoxy) and haloC$_{1-4}$alkyl (e.g., trifluoromethyl);

1.7 Formula I or any of 1.1-1.4, wherein R$_4$ is aryl (e.g., phenyl) substituted with C$_{1-4}$alkyl (e.g., ethyl);

1.8 Formula I or any of 1.1-1.4, wherein R$_4$ is aryl (e.g., phenyl) substituted with C$_{3-7}$cycloalkyl (e.g., cyclopropyl);

1.9 Formula I or any of 1.1-1.4, wherein R$_4$ is aryl (e.g., phenyl) substituted with C$_{1-4}$alkoxy (e.g., methoxy);

1.10 Formula I or any of 1.1-1.4, wherein R$_4$ is aryl (e.g., phenyl) substituted with haloC$_{1-4}$alkyl (e.g., trifluoromethyl);

1.11 Formula I or any of 1.1-1.10, wherein R$_6$ is H or C$_{1-4}$alkyl (e.g., methyl);

1.12 Formula I or any of 1.1-1.10, wherein R$_6$ is C$_{1-4}$alkyl (e.g., methyl);

1.13 any of the preceding formulae, wherein the compound is selected from a group consisting of:

7-(Azetidin-1-yl)-3-methyl-1-(1-methyl-5-(4-(trifluoromethyl)phenyl)-1H-pyrazol-4-yl)-1H-pyrazolo[4,3-d]pyrimidine;

7-(Azetidin-1-yl)-1-(5-(4-methoxy-2-methylphenyl)-1-methyl-1H-pyrazol-4-yl)-3-methyl-1H-pyrazolo[4,3-d]pyrimidine;

7-(Azetidin-1-yl)-1-(5-(4-cyclopropylphenyl)-1-methyl-1H-pyrazol-4-yl)-3-methyl-1H-pyrazolo[4,3-d]pyrimidine;

7-(Azetidin-1-yl)-1-(5-(4-ethylphenyl)-1-methyl-1H-pyrazol-4-yl)-3-methyl-1H-pyrazolo[4,3-d]pyrimidine;

1.14 any of the preceding formulae wherein the compounds inhibit phosphodiesterase-mediated (e.g., PDE2-mediated) hydrolysis of cGMP, e.g., with an IC$_{50}$ of less than 1 µM, more preferably less than or equal to 250 nM, more preferably less than or equal to 10 nM in an immobilized-metal affinity particle reagent PDE assay, for example, as described in Example 5, in free or salt form.

In a second aspect, the disclosure provides a pharmaceutical composition comprising a Compound of the Disclosure, i.e., Compounds of Formula I, or any of formulae 1.1-1.14, in free or pharmaceutically acceptable salt form, in combination or association with a pharmaceutically acceptable diluents or carrier.

The disclosure also provides methods of using the Compounds of the Disclosure for treatment of PDE2-mediated disorders, e.g., disorders as set forth below (especially treatment of anxiety, depression, autism spectrum disorder (ASD), schizophrenia, cognitive impairment). This list is not intended to be exhaustive and may include other diseases and disorders as set forth below.

Therefore, in a third aspect, the disclosure provides a method for the treatment of a PDE2-mediated disorder, comprising administering to a subject in need thereof a therapeutically effective amount of a Compound of the Disclosure disclosed herein, i.e., Compounds of Formula I, or any of formulae 1.1-1.14, in free or pharmaceutically acceptable salt form, or a pharmaceutical composition disclosed herein.

In a further embodiment of the third aspect, the disclosure provides a method for the treatment of the following disorders:

neurological disorders (such as migraine; epilepsy; Alzheimer's disease; Parkinson's disease; brain injury; stroke; cerebrovascular diseases (including cerebral arteriosclerosis, cerebral amyloid angiopathy, hereditary cerebral hemorrhage, and brain hypoxia-ischemia); spinal muscular atrophy; lateral sclerosis; multiple sclerosis;

cognitive disorders (including amnesia, senile dementia, HIV associated dementia, Alzheimer's associated dementia, Huntington's associated dementia, Lewy body dementia, vascular dementia, drug related dementia, delirium, and mild cognitive impairment); cognitive dysfunction associated with Parkinson's disease and depression;

mental deficiency (including Down syndrome and fragile X syndrome);

sleep disorders (including hypersomnia, circadian rhythm sleep disorder, insomnia, parasomnia, and sleep deprivation);

psychiatric disorders (such as anxiety (including acute stress disorder, generalized anxiety disorder, social anxiety disorder, panic disorder, post-traumatic stress disorder (PTSD), obsessive-compulsive disorder, specific phobia, social phobia, chronic anxiety disorder and obsessive compulsive disorder,);

factitious disorder (including acute hallucinatory mania);

impulse control disorders (including pathological gambling, pathological fire-setting, pathological stealing and intermittent explosive disorder);

mood disorders (including bipolar I disorder, bipolar II disorder, mania, mixed affective state, major depression, chronic depression, seasonal depression, psychotic depression and postpartum depression);

psychomotor disorders (extrapyraamidal and movement disorders, e.g., Parkinsonism, Lewy body disease, tremor, drug-induced tremor, drug-induced tardive dyskineisa, L-dopa-induced dyskinesia and restless leg syndrome);

psychotic disorders (including schizophrenia (e.g., continuous or episodic, paranoid, hebephrenic, catatonic, undifferentiated and residual schizophrenic disorders), schizoaffective disorder, schizophreniform, and delusional disorder);

drug dependence (including narcotic dependence, alcoholism, amphetamine dependence, cocaine addiction, nicotine dependence, and drug withdrawal syndrome);

eating disorders (including anorexia, bulimia, binge eating disorder, hyperphagia, and pagophagia);

pediatric psychiatric disorders (including attention deficit disorder, attention deficit/hyperactive disorder, conduct disorder (e.g., tic disorders such as transient, chronic, motor or vocal tic disorders), autism and autism spectrum disorder (ASD));

mental and behavioral disorders due to psychoactive substance use;

cardiovascular disorder (e.g., pulmonary hypertension and pulmonary arterial hypertension); and pain (e.g., bone and joint pain (osteoarthritis), repetitive motion pain, dental pain, cancer pain, myofascial pain (muscular injury, fibromyalgia), perioperative pain (general surgery, gynecological), chronic pain and neuropathic pain), in a subject, preferably a mammal, preferably a human, comprising administering to said subject a therapeutically effective amount of a Compound of the Disclosure disclosed herein, i.e., Compounds of Formula I, or any of formulae 1.1-1.14, in free or pharmaceutically acceptable salt form, or a pharmaceutical composition disclosed herein.

In one embodiment, the disease or disorder is selected from a group consisting of anxiety, depression, autism spectrum disorder and schizophrenia, for example anxiety and/or depression in autistic and/or schizophrenic patients.

In another embodiment, the disease or disorder is cognitive impairment associated with schizophrenia or dementia.

In the fourth aspect, the disclosure provides a Compound of the Disclosure disclosed herein, i.e., Compounds of Formula I, or any of formulae 1.1-1.14, in free or pharmaceutically acceptable salt form (for use in the manufacture of a medicament) for the treatment of a PDE2-mediated disorder as disclosed herein.

In the fifth aspect, the disclosure provides a pharmaceutical composition comprising a Compound of the Disclosure disclosed herein, i.e., Compounds of Formula I, or any of formulae 1.1-1.14, in free or pharmaceutically acceptable salt form, in combination or association with a pharmaceutically acceptable diluents or carrier, for use in the treatment of a PDE2-mediated disorder as disclosed herein.

BRIEF DESCRIPTION OF THE DRAWINGS

FIG. 1 illustrats the plasma and brain levels in mice dosed with 10 mg/kg P.O. of the compound of Example 1 over time.

DETAILED DESCRIPTION OF THE INVENTION

If not otherwise specified or clear from context, the following terms herein have the following meanings:
(a) "Alkyl" as used herein is a saturated or unsaturated hydrocarbon moiety, preferably saturated, preferably having one to six carbon atoms, preferably having one to four carbon atoms, which may be linear or branched, and may be optionally mono-, di- or tri-substituted, e.g., with halogen (e.g., chloro or fluoro), hydroxy, or carboxy.
(b) "Aryl" as used herein is a mono or bicyclic aromatic hydrocarbon, preferably phenyl, optionally substituted, e.g., with alkyl (e.g., methyl), halogen (e.g., chloro or fluoro), haloalkyl (e.g., trifluoromethyl) or hydroxy.
(c) "Heteroaryl" as used herein is an aromatic moiety wherein one or more of the atoms making up the aromatic ring is sulfur or nitrogen rather than carbon, e.g., pyridyl or thiadiazolyl, which may be optionally substituted, e.g., with alkyl, halogen, haloalkyl or hydroxy.

Compounds of the Disclosure, e.g., Compounds of Formula I, or any of formulae 1.1-1.14, may exist in free or salt form, e.g., as acid addition salts. In this specification unless otherwise indicated, language such as "Compounds of the Disclosure" is to be understood as embracing the compounds in any form, for example free or acid addition salt form, or where the compounds contain acidic substituents, in base addition salt form. The Compounds of the Disclosure are intended for use as pharmaceuticals, therefore pharmaceutically acceptable salts are preferred. Salts which are unsuitable for pharmaceutical uses may be useful, for example, for the isolation or purification of free Compounds of the Disclosure or their pharmaceutically acceptable salts, are therefore also included.

Compounds of the Disclosure may in some cases also exist in prodrug form. A prodrug form is compound which converts in the body to a Compound of the Disclosure. For example when the Compounds of the Disclosure contain hydroxy or carboxy substituents, these substituents may form physiologically hydrolysable and acceptable esters. As used herein, "physiologically hydrolysable and acceptable ester" means esters of Compounds of the Disclosure which are hydrolysable under physiological conditions to yield acids (in the case of Compounds of the Disclosure which have hydroxy substituents) or alcohols (in the case of Compounds of the Disclosure which have carboxy substituents) which are themselves physiologically tolerable at doses to be administered. Therefore, wherein the Compound of the Disclosure contains a hydroxy group, for example, Compound-OH, the acyl ester prodrug of such compound, i.e., Compound-O—C(O)—C$_{1-4}$alkyl, can hydrolyze in the body to form physiologically hydrolysable alcohol (Compound-OH) on the one hand and acid on the other (e.g., HOC(O)—C$_{1-4}$alkyl). Alternatively, wherein the Compound of the Disclosure contains a carboxylic acid, for example, Compound-C(O)OH, the acid ester prodrug of such compound, Compound-C(O)O—C$_{1-4}$ alkyl can hydrolyze to form Compound-C(O)OH and HO—C$_{1-4}$alkyl. As will be appreciated, the term thus embraces conventional pharmaceutical prodrug forms.

The Compounds of the Disclosure herein include their enantiomers, diastereoisomers and racemates, as well as their polymorphs, hydrates, solvates and complexes. Some individual compounds within the scope of this invention may contain double bonds. Representations of double bonds in this invention are meant to include both the E and the Z isomer of the double bond. In addition, some compounds within the scope of this invention may contain one or more asymmetric centers. This invention includes the use of any of the optically pure stereoisomers as well as any combination of stereoisomers.

It is also intended that the Compounds of the Disclosure encompass their stable and unstable isotopes. Stable isotopes are nonradioactive isotopes which contain one additional neutron compared to the abundant nuclides of the same species (i.e., element). It is expected that the activity of compounds comprising such isotopes would be retained, and such compound would also have utility for measuring pharmacokinetics of the non-isotopic analogs. For example, the hydrogen atom at a certain position on the Compounds of the Disclosure may be replaced with deuterium (a stable isotope which is non-radioactive). Examples of known stable isotopes include, but not limited to, deuterium, $^{13}$C, $^{15}$N, $^{18}$O. Alternatively, unstable isotopes, which are radioactive isotopes which contain additional neutrons compared to the abundant nuclides of the same species (i.e., element), e.g., $^{123}$I, $^{131}$I, $^{125}$I, $^{11}$C, $^{18}$F, may replace the corresponding abundant species of I, C and F. Another example of useful isotope of the compound of the invention is the $^{11}$C isotope. These radio isotopes are useful for radio-imaging and/or pharmacokinetic studies of the compounds of the invention. Isotopically-labeled compounds of Formula I may generally be prepared by carrying out by substituting an isotopically-labeled reagent for a non-isotopically-labeled reagent.

The phrase "Compounds of the Disclosure" or "PDE 2 inhibitors of the Disclosure" encompasses any and all of the compounds disclosed herewith, e.g., a Compounds of Formula I, or any of formulae 1.1-1.14, as hereinbefore described, in free or salt form.

The words "treatment" and "treating" are to be understood accordingly as embracing treatment or amelioration of symptoms of the disease as well as treatment of the cause of the disease. In one embodiment, the invention provides a method for the treatment of the disease or disorder disclosed herein. In another embodiment, the invention provides a method for the prophylaxis of a disease or disorder as disclosed herein.

For methods of treatment, the word "effective amount" is intended to encompass a therapeutically effective amount to treat a specific disease or disorder.

The term "pulmonary hypertension" is intended to encompass pulmonary arterial hypertension.

The term "subject" includes human or non-human (i.e., animal). In particular embodiment, the invention encompasses both human and nonhuman. In another embodiment, the invention encompasses nonhuman. In other embodiment, the term encompasses human.

The term "comprising" as used in this disclosure is intended to be open-ended and does not exclude additional, unrecited elements or method steps.

The term "cognitive disorders" refers to any disorder comprising a symptom of cognitive deficiency (i.e., subnormal or suboptimal functioning in one or more cognitive aspects such as memory, intellect, learning, logic, attention or executive function (working memory) in an individual compared to other individuals within the same general age population). Therefore, cognitive disorders include but are not limited to amnesia, senile dementia, HIV associated dementia, Alzheimer's associated dementia, Huntington's associated dementia, Lewy body dementia, vascular dementia, drug related dementia, delirium, and mild cognitive impairment. Cognitive disorders can also be a disorder primarily but not exclusively related to psychosis (schizophrenia), mood disorders, bipolar disorders, stroke, frontotemporal dementia, progressive supranuclear palsy, cerebral trauma and drug abuse, Asperger's syndrome and age-associated memory impairment.

Compounds of the Disclosure, e.g., Compounds of Formula I, or any of formulae 1.1-1.14, as hereinbefore described, in free or pharmaceutically acceptable salt form may be used as a sole therapeutic agent, but may also be used in combination or for co-administration with other active agents.

Dosages employed in practicing the present invention will of course vary depending, e.g. on the particular disease or condition to be treated, the particular Compound of the Disclosure used, the mode of administration, and the therapy desired. Compounds of the Disclosure may be administered by any suitable route, including orally, parenterally, transdermally, or by inhalation, but are preferably administered orally. In general, satisfactory results, e.g. for the treatment of diseases as hereinbefore set forth are indicated to be obtained on oral administration at dosages of the order from about 0.01 to 2.0 mg/kg. In larger mammals, for example humans, an indicated daily dosage for oral administration will accordingly be in the range of from about 0.75 to 150 mg, conveniently administered once, or in divided doses 2 to 4 times, daily or in sustained release form. Unit dosage forms for oral administration thus for example may comprise from about 0.2 to 75 or 150 mg, e.g. from about 0.2 or 2.0 to 50, 75 or 100 mg of a Compound of the Disclosure, together with a pharmaceutically acceptable diluent or carrier therefor.

Pharmaceutical compositions comprising Compounds of the Disclosure may be prepared using conventional diluents or excipients and techniques known in the galenic art. The pharmaceutically acceptable carrier may comprise any conventional pharmaceutical carrier or excipient. Suitable pharmaceutical carriers include inert diluents or fillers, water and various organic solvents (such as hydrates and solvates). The pharmaceutical compositions may, if desired, contain additional ingredients such as flavorings, binders, excipients and the like. Thus for oral administration, tablets containing various excipients, such as citric acid, may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Non-limiting examples of materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof. The pharmaceutical composition may, for example, be in a form suitable for oral administration as a tablet, capsule, pill, powder, sustained release formulation, solution or suspension, for parenteral injection as a sterile solution, suspension or emulsion, for topical administration as an ointment or cream or for rectal administration as a suppository.

The compounds of the Disclosure herein and their pharmaceutically acceptable salts may be made using the methods as described and exemplified herein and by methods similar thereto and by methods known in the chemical art. Such methods include, but not limited to, those described below. If not commercially available, starting materials for these processes may be made by procedures, which are selected from the chemical art using techniques which are similar or analogous to the synthesis of known compounds. All references cited herein are hereby incorporated by reference in their entirety.

Example 1

7-(Azetidin-1-yl)-3-methyl-1-(1-methyl-5-(4-(trifluoromethyl)phenyl)-1H-pyrazol-4-yl)-1H-pyrazolo[4,3-d]pyrimidine

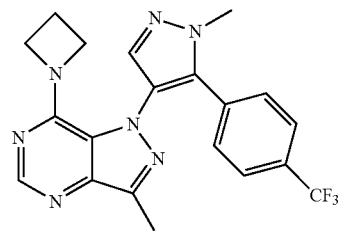 [SMILES: Cc1nn(-c2cnn(C)c2-c2ccc(C(F)(F)F)cc2)c2c(N3CCC3)ncnc12]

(a) 5-Chloro-1-methyl-4-nitro-1H-pyrazole

Lithium bis(trimethylsilyl)amide (1.0 M, 65 mL, 65 mmol) in THF is added dropwise into a solution of 1-methyl-4-nitro-1H-pyrazole (5.50 g, 43.3 mmol) and hexachloroethane (10.54 g, 44.5 mmol) in methylene chloride (120 mL) at 25° C. The reaction mixture is stirred at 25° C. for 60 min, and then quenched with water (1 mL). The mixture is evaporated to dryness. The residue is washed with water (50 mL), sat. NaHCO$_3$ two times (2×30 mL) and brine (30 mL) successively, and then dried under vacuum to give 6.50 g of product (93% yield). MS (ESI) m/z 162.0 [M+H]$^+$. $^1$H NMR (500 MHz, CDCl$_3$) δ 8.15 (s, 1H), 3.92 (s, 3H).

(b) 5-Chloro-1-methyl-1H-pyrazol-4-amine hydrochloride

To a suspension of 5-chloro-1-methyl-4-nitro-1H-pyrazole (6.50 g, 40.2 mmol) in 12 N HCl (15 mL) and ethanol (15 mL) is added tin(II) chloride (35.5 g, 160.9 mmol). The reaction mixture is stirred at 90° C. until the reaction is complete. The reaction mixture is evaporated to dryness. The residue is treated with 12 N HCl (25 mL) and then cooled at 5° C. for 2 h. After filtration, the filter cake is washed with 6 N HCl (2×25 mL) and then dried under vacuum to give 6.08 g of product (yield: 90%). MS (ESI) 132.0 [M+H]$^+$. $^1$H NMR (500 MHz, CD$_3$OD) δ 7.66 (s, 1H), 3.89 (s, 3H).

(c) 5-Chloro-4-hydrazinyl-1-methyl-1H-pyrazole hydrochloride

To a stirred solution of 5-chloro-1-methyl-1H-pyrazol-4-amine hydrochloride (6.08 g, 36.2 mmol) in HCl (12 N, 35 mL) is added aqueous NaNO$_2$ (5.50 g, 80.0 mmol) at 0° C. The reaction mixture is stirred at 0° C. for 45 min and then tin (II) chloride (22.8 g, 120 mmol) is added. After the completion of the addition, the reaction mixture is stirred at 0° C. for 30 min and then stirred at room temperature overnight. The resulting mixture is cooled in an ice bath for 2 h and then filtered. The filter cake is washed with HCl (12 N, 20 mL) and then dried under vacuum to give 7.77 g of crude product (yield: 98%), which is used in the next reaction without further purification. MS (ESI) m/z 147.0 [M+H]$^+$.

(d) 5-Bromo-4-chloro-6-(1-ethoxyvinyl)pyrimidine

A suspension of 5-bromo-4,6-dichloropyrimidine (5.00 g, 21.9 mmol) and tributyl(1-ethoxyvinyl)stannane (7.92 g, 21.9 mmol) in DMF (20 mL) is degassed with argon and then tetrakis(triphenylphosphine) palladium(0) (1.27 mg, 1.10 mmol) is added. The suspension is degassed again, and then heated at 110° C. under argon for 8 h. After solvents are removed under reduced pressure, the residue is purified by silica gel column chromatography eluting with a gradient of 0-40% ethyl acetate in hexanes over 30 min to give 2.72 g of product (yield: 47%). MS (ESI) m/z 263.0 [M+H]$^+$. $^1$H NMR (500 MHz, CDCl$_3$) δ 8.85 (s, 1H), 4.71 (d, J=3.1 Hz, 1H), 4.60 (d, J=3.1 Hz, 1H), 3.98 (q, J=7.0 Hz, 2H), 2.67 (s, OH), 1.42 (t, J=7.0 Hz, 3H).

(e) 5-Bromo-4-chloro-6-(1-(2-(5-chloro-1-methyl-1H-pyrazol-4-yl)hydrazono)ethyl)pyrimidine A suspension of 5-bromo-4-chloro-6-(1-ethoxyvinyl)pyrimidine (1.60 g, 6.07 mmol) and 5-chloro-4-hydrazinyl-1-methyl-1H-pyrazole hydrochloride (3.11 g, 12.1 mmol) in acetic acid (32 mL) is stirred at 60° C. for 6 h. After the solvent is removed under reduced pressure, the residue is treated with sat. NaHCO$_3$ (40 mL), and then extracted with ethyl acetate (3×100 mL). The combined organic phase is washed with brine (70 mL) and then evaporated to dryness. The residue is dried under vacuum to give 1.0 g of crude product (yield: 45%), which is used in the next step without further purification. MS (ESI) m/z 362.9 [M+H]$^+$. $^1$H NMR (500 MHz, CDCl$_3$) δ 8.79 (s, 1H), 7.66 (s, 1H), 7.05 (s, 1H), 3.83 (s, 3H), 2.32 (s, 3H).

(f) 7-Chloro-1-(5-chloro-1-methyl-1H-pyrazol-4-yl)-3-methyl-1H-pyrazolo[4,3-d]pyrimidine A mixture of 5-bromo-4-chloro-6-(1-(2-(5-chloro-1-methyl-1H-pyrazol-4-yl)hydrazono)ethyl)pyrimidine (334 mg, 0.92 mmol), 1,10-phenanthroline (497 mg, 2.76 mmol) and K$_2$CO$_3$ (127 mg, 0.92 mmol) in toluene (4 mL) in a sealed tube is heated at 100° C. for 1.5 h. After cooled to room temperature, the reaction mixture is diluted with toluene (3 mL) and then filtered. The solid is washed with toluene two times (2×3 mL). The combined filtrate is washed with saturated FeSO$_4$.7H$_2$O three times (3×4 mL) and then evaporated to dryness. The obtained residue is further dried under vacuum to give 147 mg of crude product (yield: 57%), which is used in the next step without further purification. MS (ESI) m/z 283.0 [M+H]$^+$.

(g) 7-(Azetidin-1-yl)-1-(5-chloro-1-methyl-1H-pyrazol-4-yl)-3-methyl-1H-pyrazolo[4,3-d]pyrimidine A mixture of 7-chloro-1-(5-chloro-1-methyl-1H-pyrazol-4-yl)-3-methyl-1H-pyrazolo[4,3-d]pyrimidine (147 mg, 0.52 mmol), azetidine hydrochloride (64 mg, 0.68 mmol), and Et$_3$N (105 mg, 1.04 mmol) in toluene (1.5 mL) in a sealed tube is stirred at room temperature until the reaction is complete. The mixture is poured into 2 N NaOH (18 mL) and then extracted with CH$_2$Cl$_2$ three times (3×25 mL). The combined organic phase is washed with brine (20 mL) and then evaporated to dryness. The obtained residue is further dried under vacuum to give 181 g of crude product, which is used in the next step without further purification. MS (ESI) 304.1 [M+H]$^+$. $^1$H NMR (500 MHz, CDCl$_3$) δ 8.51 (s, 1H), 7.66 (s, 1H), 3.95 (s, 3H), 3.87 (t, J=7.8 Hz, 4H), 2.61 (s, 3H), 2.33-2.25 (m, 2H).

(h) 7-(Azetidin-1-yl)-3-methyl-1-(1-methyl-5-(4-(trifluoromethyl)phenyl)-1H-pyrazol-4-yl)-1H-pyrazolo[4,3-d]pyrimidine A suspension of 7-(azetidin-1-yl)-1-(5-chloro-1-methyl-1H-pyrazol-4-yl)-3-methyl-1H-pyrazolo[4,3-d]pyrimidine (58 mg, 0.19 mmol), 4-(trifluoromethyl)-phenylboronic acid (51 mg, 0.27 mmol) and tripotassium phosphate (92 mg, 0.43 mmol) in ethanol (0.70 mL) and water (0.080 mL) is heated at 70° C. under argon for 10 min and then tetrakis (triphenylphosphine) palladium(0) (19 mg, 0.017 mmol) is added. The suspension is degassed again and then heated in a microwave at 130° C. for 2 h. Additional tetrakis(triphenylphosphine) palladium(0) (9 mg, 0.0079 mmol) is added. The mixture is heated in the microwave at 140° C. for 7 h. After the solvents are removed, the residue is purified with a semi-preparative HPLC using a gradient of 0-33% acetonitrile in water containing 0.1% formic acid over 16 min give 12 mg of the final product as off white solids (HPLC purity: 98%; yield: 15%). MS (ESI) m/z 414.2 [M+H]$^+$. $^1$H NMR (500 MHz, CDCl$_3$) δ 8.43 (s, 1H), 7.71 (s, 1H), 7.63 (d, J=8.1 Hz, 2H), 7.50 (d, J=8.1 Hz, 2H), 3.96 (s, 3H), 3.81 (t, J=7.8 Hz, 4H), 2.59 (s, 3H), 2.32-2.21 (m, 2H).

Example 2

7-(Azetidin-1-yl)-1-(5-(4-methoxy-2-methylphenyl)-1-methyl-1H-pyrazol-4-yl)-3-methyl-1H-pyrazolo[4,3-d]pyrimidine

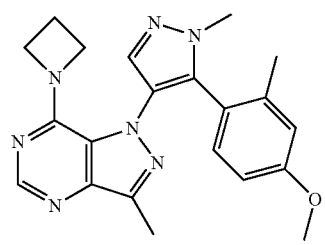 [SMILES: COc1ccc(-c2c(-n3nc(C)c4ncnc(N5CCC5)c43)cnn2C)c(C)c1]

The title compound is prepared in an analogous fashion following the procedure described in the synthesis of Example 1 wherein 4-methoxy-2-methylphenylboronic acid and $K_2CO_3$ are added in the final step instead of 4-(trifluoromethyl)phenylboronic acid and $K_3PO_4$, respectively. Final product is obtained as off white solids (HPLC purity: 99%; yield: 32%). MS (ESI) m/z 390.2 [M+H]$^+$. $^1$H NMR (500 MHz, CDCl$_3$) δ 8.37 (s, 1H), 7.77 (s, 1H), 7.06 (d, J=8.4 Hz, 1H), 6.68 (d, J=2.5 Hz, 1H), 6.64 (dd, J=8.5, 2.6 Hz, 1H), 4.04-3.82 (m, 4H), 3.74 (s, 3H), 3.71 (s, 3H), 2.55 (s, 3H), 2.35-2.26 (m, 2H), 2.08 (s, 3H).

Example 3

7-(Azetidin-1-yl)-1-(5-(4-cyclopropylphenyl)-1-methyl-1H-pyrazol-4-yl)-3-methyl-1H-pyrazolo[4,3-d]pyrimidine

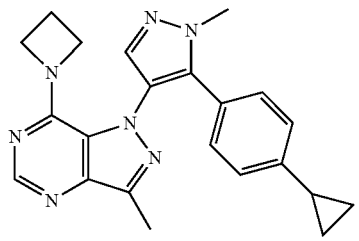 [SMILES: Cc1nn(-c2cnn(C)c2-c2ccc(C3CC3)cc2)c2c(N3CCC3)ncnc12]

The title compound is prepared in an analogous fashion following the procedure described in the synthesis of Example 1 wherein cyclopropylphenyl-boronic acid and $Na_2CO_3$ are added in the final step instead of 4-(trifluoromethyl)phenylboronic acid and $K_3PO_4$, respectively. MS (ESI) m/z 386.2 [M+H]$^+$.

Example 4

7-(Azetidin-1-yl)-1-(5-(4-ethylphenyl)-1-methyl-1H-pyrazol-4-yl)-3-methyl-1H-pyrazolo[4,3-d]pyrimidine

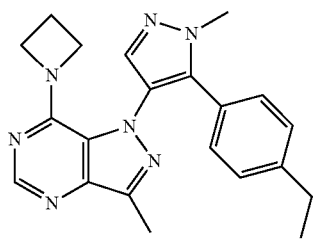 [SMILES: CCc1ccc(-c2c(-n3nc(C)c4ncnc(N5CCC5)c43)cnn2C)cc1]

The title compound is prepared in an analogous fashion following the procedure described in the synthesis of Example 1 wherein 4-ethylphenyl-boronic acid and $Cs_2CO_3$ are added in the final step instead of 4-(trifluoromethyl) phenylboronic acid and $K_3PO_4$, respectively. MS (ESI) m/z 374.2 [M+H]$^+$.

Example 5

Measurement of PDE2 Inhibition In Vitro r-hPDE2A (Accession No. NM_002599, *Homo sapiens* phosphodiesterase 2A, cGMP-stimulated, transcript variant 1) A mammalian expression cloning vector with recombinant cDNA copy of the gene is purchased from Origene. Protein is expressed via transient transfection of HEK293 cells. The cells are harvested at 48 hours after transfection, washed once with TBS buffer (50 mM Tris-HCl, pH 7.5, 150 mM NaCl), then lysed by sonication in cold homogenization buffer (50 mM Tris-HCl, pH 7.5, 5 mM $MgCl_2$, lx protease inhibitor cocktail). The homogenate is centrifuged for 30 mM at 15,000 g at 4° C. to obtain the soluble cytosolic fraction. The protein concentration of the cytosol is determined using BCA Protein Assay Kit (Pierce) with bovine serum albumin as a standard.

Assay:

PDE2A is assayed with FL-cAMP as substrate. An enzyme titration is first performed to determine the working concentration of PDE. The concentration of the enzyme giving activity of 100 ΔmP in the absence of inhibitor is deemed an appropriate working concentration for PDE.

PDE enzyme is diluted in a standard reaction buffer (10 mM Tris-HCl pH 7.2, 10 mM $MgCl_2$, 0.1% BSA, 0.05% $NaN_3$) according to the titration curve. For PDE2 assay the reaction buffer is supplemented with 1 µM cGMP to fully activate the enzyme. 99 µl of diluted enzyme solution is added into each well in a flat bottom 96-well polystyrene plate and then 1 µl of test compound dissolved in 100% DMSO is added. The compounds are mixed and pre-incubated with the enzyme for 10 min at room temperature.

The FL-cNMP conversion reaction is initiated by addition of substrate (45 nM final). Enzyme and inhibitor mix (16 µl) and substrate solution (4 µl of 0.225 µM) are combined in a 384-well microtiter plate. The reaction is incubated in the dark at room temperature for 15 min. The reaction is halted by addition of 60 µl of binding reagent (1:400 dilution of IMAP beads in binding buffer supplemented with 1:1800 dilution of antifoam) to each well of the 384-well plate. The plate is incubated at room temperature for 1 hour to allow IMAP binding to proceed to completion, and then placed in an Envision multimode microplate reader (PerkinElmer, Shelton, Conn.) to measure the fluorescence polarization (Δmp).

A decrease in cAMP concentration, measured as decreased Amp, is indicative of inhibition of PDE activity. IC$_{50}$ values are determined by measuring enzyme activity in the presence of 8 to 16 concentrations of compound ranging from 0.00037 nM to 80,000 nM and then plotting drug concentration versus ΔmP Test well values are normalized to control reactions run on the same plate (values converted to % of control). IC$_{50}$ values are estimated using nonlinear regression software, fitting a four-parameter one-site dose-response model (XLFit; IDBS, Cambridge, Mass.). Bottom of curve is fixed at 0% of control.

Quality Controls:

To determine the IC50 of an inhibitor, an enzyme concentration that gave optimal signal range of 100-200 millipolarization units is selected. The total fluorescence intensity of each sample well is measured to calculate the average and standard deviation. If the total fluorescence intensity of any sample well is not within the range of Average±3SD, the mp value of that particular well is discarded.

Using the IMAP procedure described or similarly described above, we screened a proprietary PDE-focused compound library to identify novel compounds with nanomolar PDE2 inhibitory activities. The exemplified compounds of the Disclosure (e.g. compounds of Examples 1-4) are tested and shown be active at nanomolar concentrations, e.g., as follows: Example 1: IC$_{50}$ 23.1 nM; Example 2: IC$_{50}$ 92 nM; Example 3: IC$_{50}$ 9.5 nM; Example 4, IC$_{50}$ 18.5 nM.

The compounds are moreover selective for PDE2; the compound of Example 4 is tested and shown to be selective for PDE2 over PDE1, PDE3, PDE4D, PDE5, PDE6, PDE7B, PDE8A, PDE9A, PDE10A and PDE11A by greater than 20-fold.

Example 6

Pharmacokinetic Study in Mice

Mice are given a single oral dose of the compound to be tested (10 mg/kg, PO) and plasma and brain availability are measured (0.25-4h) using HPLC and LC-MS using methods analogous to those described in Zhao et al., *J. Chromatogr. B. Analyt. Technol. Biomed. Life Sci.* (2005) 819(1):73-80 and Appels, N. M., et al., *Rapid Commun. Mass Spec.* 2005. 19(15): p. 2187-92. The experiment shows that the compound of Example 1 has good brain access as shown in FIG. 1.

Example 7

The Effects of Treatment with PDE2 Inhibitors on Memory Performance of Wistar Rats in the Object Recognition Task The memory-enhancing effects of the compound of Example 1 are tested in an animal model of cognition, the object recognition task. See, Ennaceur, A., Delacour, J., 1988. A new one-trial test for neurobiological studies of memory in rats. 1: Behavioral data. Behav. Brain Res. 31, 47-59. Rats remember which object they have explored in a previous trial when they are tested one hour later. However, when a 24 h inter-trial interval is used, they are not able to remember which object was presented to them in the first trial. It is tested whether the compound of Example 1 would attenuate this time-induced object memory deficit, when given 2 h before the first trial. The compounds are given to 2-3-months-old male Wistar rats.

The compound of Example 1 is injected orally (2 ml/kg) 2 h before learning, at doses of 0, 0.3, 1, 3 and 10 mg/kg. None of the tested doses have an effect on exploratory behavior. The present study shows that the compound of Example 1 is able to completely prevent the time-dependent forgetting at a dose of 1.0 mg/kg. An intermediate memory improvement is found for 0.3 and 3.0 mg/kg.

Example 8

Effects of Novel PDE2 Inhibitors on cGMP Signaling in Hippocampal Cells and in Brain We propose that HT-22 cells (immortalized mouse hippocampal-neuronal precursor cells sub-cloned from their parent HT-4 cells) are a valuable model for understanding the cellular and molecular processes relevant to hippocampus-dependent emotional changes. We anticipate that Aim 1 will yield 10-20 novel PDE2 inhibitors for functional evaluation in cell-based assays. Only compounds that induce a significant increase in cGMP accumulation in cell-based HT-22 cell assays will advance to behavioral evaluation. The cell-based assay data would be a minimal requirement for any PDE2 inhibitor with potential use for CNS indications and will provide guidance for dose selection for behavioral testing.

What is claimed is:

1. A Compound of Formula I

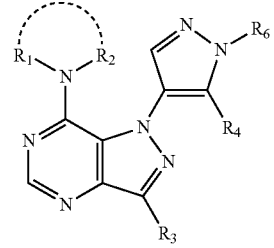

Formula I wherein
(i) $R_1$ and $R_2$ together with the nitrogen atom form an azetidine-1-yl;
(ii) $R_3$ is methyl;
(iii) $R_4$ is heteroaryl or aryl optionally substituted with one or more groups selected from $C_{1-4}$alkyl, $C_{3-7}$cycloalkyl, $C_{1-4}$alkoxy and halo$C_{1-4}$alkyl;
(iv) $R_6$ is methyl;
in free or salt form.

2. The compound according to claim 1, wherein $R_4$ is aryl-optionally substituted with one or more groups selected from $C_{1-4}$alkyl, $C_{3-7}$cycloalkyl, $C_{1-4}$alkoxy and halo$C_{1-4}$alkyl, in free or salt form.

3. The compound according to claim 1, wherein $R_4$ is aryl substituted with one or more groups selected from $C_{1-4}$alkyl, $C_{3-7}$cycloalkyl, $C_{1-4}$alkoxy and halo$C_{1-4}$alkyl, in free or salt form.

4. The compound according to claim 1, wherein the compound is selected from the group consisting of:
   7-(Azetidin-1-yl)-3-methyl-1-(1-methyl-5-(4-(trifluoromethyl)phenyl)-1H-pyrazol-4-yl)-1H-pyrazolo[4,3-d]pyrimidine;
   7-(Azetidin-1-yl)-1-(5-(4-methoxy-2-methylphenyl)-1-methyl-1H-pyrazol-4-yl)-3-methyl-1H-pyrazolo[4,3-d]pyrimidine;
   7-(Azetidin-1-yl)-1-(5-(4-cyclopropylphenyl)-1-methyl-1H-pyrazol-4-yl)-3-methyl-1H-pyrazolo[4,3-d]pyrimidine;
   7-(Azetidin-1-yl)-1-(5-(4-ethylphenyl)-1-methyl-1H-pyrazol-4-yl)-3-methyl-1H-pyrazolo[4,3-d]pyrimidine;
in free or salt form.

5. A pharmaceutical composition comprising a compound according to claim 1, in combination or association with a pharmaceutically acceptable diluents or carrier.

6. A pharmaceutical composition comprising a compound according to claim 4, in combination or association with a pharmaceutically acceptable diluent or carrier.

7. A method for the treatment of a PDE2 mediated disorder comprising administering to a subject in need thereof an effective amount of a compound according to claim 1, wherein the disorder is selected from the group consisting of anxiety, depression, amnesia, dementias and mild cognitive impairment, pulmonary hypertension, pulmonary arterial hypertension and heart failure.

8. The method of claim 7, wherein the disorder is selected from amnesia, senile dementia, HIV associated dementia, Alzheimer's associated dementia, Huntington's associated dementia, Lewy body dementia, vascular dementia, drug related dementia, delirium, and mild cognitive impairment.

* * * * *